US008187258B2

(12) United States Patent
Teiwes et al.

(10) Patent No.: US 8,187,258 B2
(45) Date of Patent: May 29, 2012

(54) APPARATUS FOR DETERMINATION AND DECREASE OF DYNAMIC POSITIONING ERRORS OF AN ABLATING LASER DURING REFRACTIVE LASER SURGERY

(75) Inventors: Winfried Teiwes, Teltow/Berlin (DE); Michael Huppertz, Teltow/Berlin (DE); Ralf Weise, Teltow/Berlin (DE); Jörg Jacobs, Teltow/Berlin (DE)

(73) Assignee: SensoMotoric Instruments Gesellschaft fuer Innovative Sensorik mbH, Teltow (DE)

( * ) Notice: Subject to any disclaimer, the term of this patent is extended or adjusted under 35 U.S.C. 154(b) by 465 days.

(21) Appl. No.: 10/276,768

(22) PCT Filed: May 21, 2001

(86) PCT No.: PCT/EP01/05837
§ 371 (c)(1),
(2), (4) Date: Nov. 19, 2002

(87) PCT Pub. No.: WO01/89438
PCT Pub. Date: Nov. 29, 2001

(65) Prior Publication Data
US 2003/0144651 A1   Jul. 31, 2003

Related U.S. Application Data

(60) Provisional application No. 60/206,104, filed on May 20, 2000.

(51) Int. Cl.
*A61F 9/0008* (2006.01)
(52) U.S. Cl. .................................. 606/12; 606/5; 606/10
(58) Field of Classification Search .......... 606/5, 10–13, 606/4–6
See application file for complete search history.

(56) References Cited

U.S. PATENT DOCUMENTS 5,980,513 A * 11/1999 Frey et al. ........................ 606/10
6,099,522 A *  8/2000 Knopp et al. .................... 606/10

FOREIGN PATENT DOCUMENTS

| DE | 42 43 021 | 4/1994 |
| DE | 19702335 | 8/1998 |
| WO | WO 95/27453 | 10/1995 |
| WO | WO 99/18868 | 4/1999 |

* cited by examiner

Primary Examiner — David Shay
(74) Attorney, Agent, or Firm — Andrew Wilford (57) ABSTRACT

The above described apparatus and methods provide the possibility to reduce or even eliminate the effects of delay between image acquisition and laser ablation. Thus this will lead to less positioning errors and therefore to better ablation results in laser refractive surgery. The importance of this invention will increase with decreasing ablating beam diameter. The use of synchronization leads to shorter delay times. Hence it follows that the duration of the whole treatment decreases as well.

10 Claims, 8 Drawing Sheets

┈┈▶ Provides with information

⟶ Triggers/ synchronizes

Clock

Fig. 6)

Fig. 7a) not synchronised

Fig. 7b) synchronised

Fig. 7c) laser triggered by eye-tracker/ scanner device

Fig. 7d) image acquisition in phase with laser

Image processing/Scanner setting
Digitizing, data transfer
Image exposure

↓ Laser Shot

Fig. 7)

Fig. 8a) pulsed illumination

Fig. 8b) electronic shutter

Fig. 8

APPARATUS FOR DETERMINATION AND DECREASE OF DYNAMIC POSITIONING ERRORS OF AN ABLATING LASER DURING REFRACTIVE LASER SURGERY

CROSS REFERENCE TO RELATED APPLICATIONS

This application is a national stage of PCT/EP 01/05839 filed 19 Nov. 2001 and is based upon U.S. provisional application 60/206,104 of 20 May 2000.

BACKGROUND OF THE INVENTION

The present invention is directed to applications for improving vision with small- or large-spot scanning refractive laser surgery of the cornea, described in greater detail in Elander, R., Rich, L. F., Robin, J. B.: "Principles and Practice of Refractive Surgery"; W. B. Saunders Company, Philadelphia; $1^{st}$ ed., 1997 and in Seiler, T.: "Refraktäre Chirurgie der Hornhaut"; Thieme, Stuttgart; $1^{st}$ ed., 2000. Here the corneal shape is adjusted by an aggregate of hundreds to thousands of laser shots in a pre-calculated ablation profile, according to the intended change of the corneal shape determined in a preceding diagnostic procedure. The temporal sequence of these laser shots is usually defined together with the ablation co-ordinates relative to the eye in a so-called shot-table before the laser treatment. During the surgery procedure the laser spot is positioned using a positioning device, for example a x-y scanner.

Figure 1:
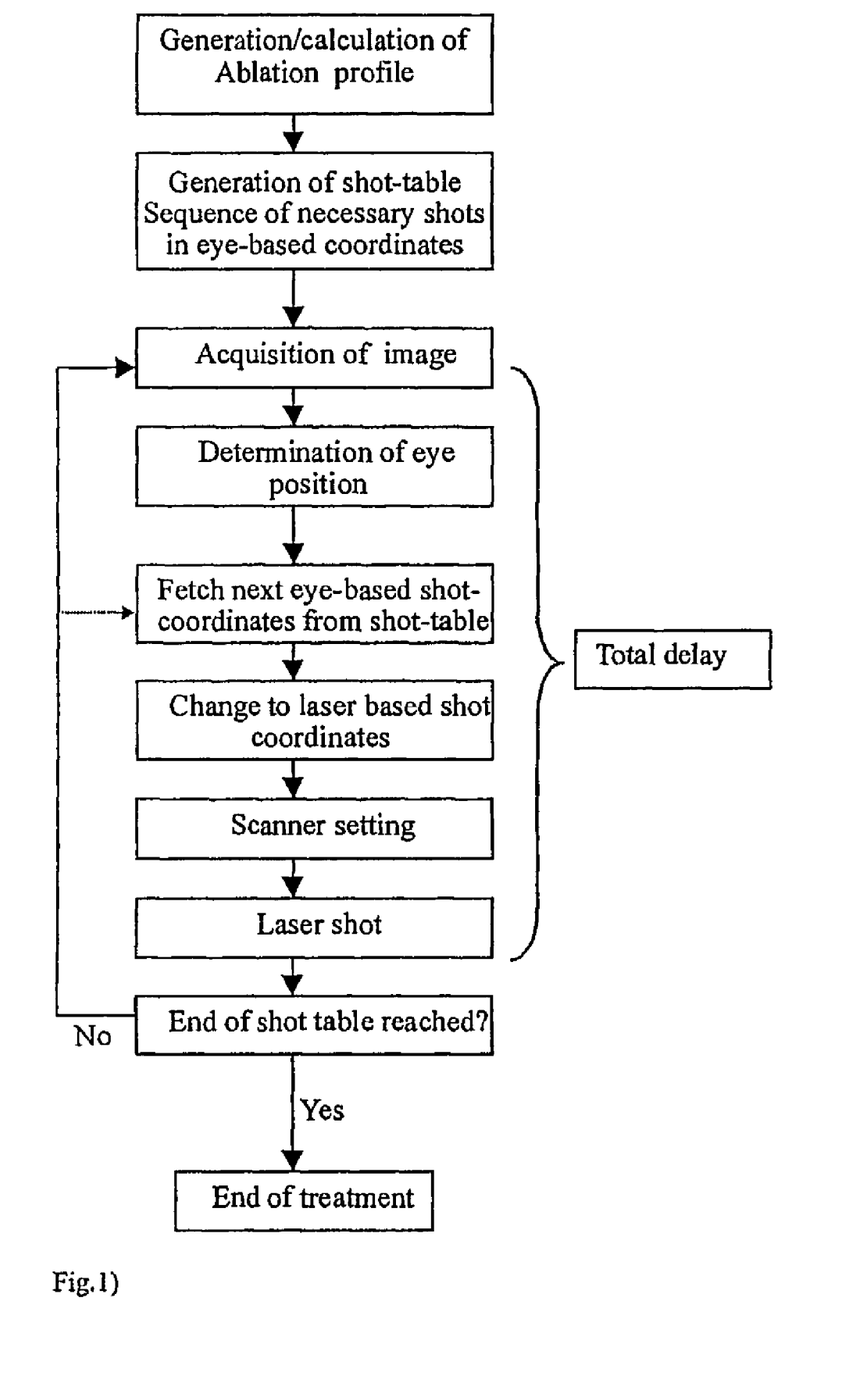
FIG. 1) Flow diagram of the standard procedure for laser refractive surgery.

So called Eye-trackers (image processing units) are commonly used to measure the exact position of the eye relative to the laser system during this procedure and to provide the eye position as correction information for the laser positioning device to compensate for the patient's eye movements before each successive laser shot is applied as described in FIG. 1.

Figure 7:
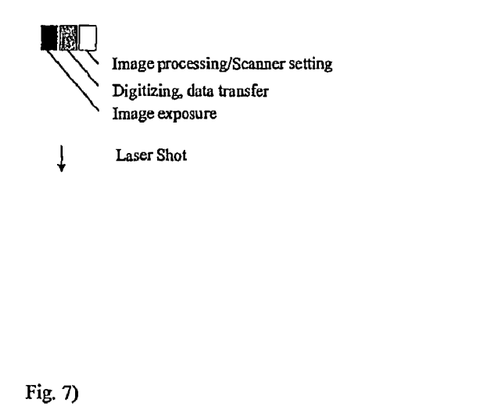
FIG. 7) Conceptual timing scheme for the different synchronization methods described in FIG. 6. Not to scale.
Figure 7A:
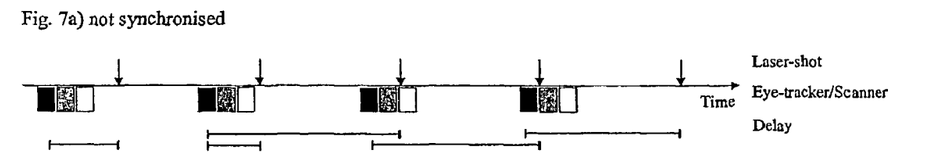

Starting at the point of time of eye position measurement (exposure time), time is required for image acquisition, data transfer, image processing to yield eye position and adjusting the positioning device to the next ablation position corrected with the eye position obtained (PROCESSING DELAY). This PROCESSING DELAY is normally in the order of tens of milliseconds. With newer high-speed systems this PROCESSING DELAY is reduced to a few milliseconds. A further delay may occur from the time completing adjustments of the positioning device until the laser shot is applied (SYNCHRONIZATION DELAY) due to missing or inaccurate synchronization of the eye tracking with the laser system. This synchronization delay can amount up to an additional period of the sampling interval for the eye tracking i.e. 16.67 ms for 60 Hz sampling of eye tracking (see FIG. 7a).

Together, both delays can lead to considerable positioning errors of laser shots onto the eye due to the patient's eye movements: During fast eye movements (saccades) which exist during the surgery procedure (although the patient is urged to fixate on a point during refractive surgery procedure) a positioning error on the cornea of up to 2 mm can occur with a common overall delay time of 50 ms. Larger errors occur only in a few percent of all laser shots, however they can result in an inaccurate corneal shape, thus imperfect vision correction.

The present invention provides methods and an apparatus for measurement and decrease of these dynamic positioning errors.

DESCRIPTION OF THE INVENTION

The present invention described below includes various techniques and methods to achieve an increase in the accuracy of positioning an ablating laser onto a moving eye, by firstly minimising the delays and resulting positioning errors and secondly by estimating or measuring positioning errors of the laser spot, correcting the resultant errors by adapting the ablation procedure, and a combination thereof.

PREFERRED EMBODIMENT

Figure 2:
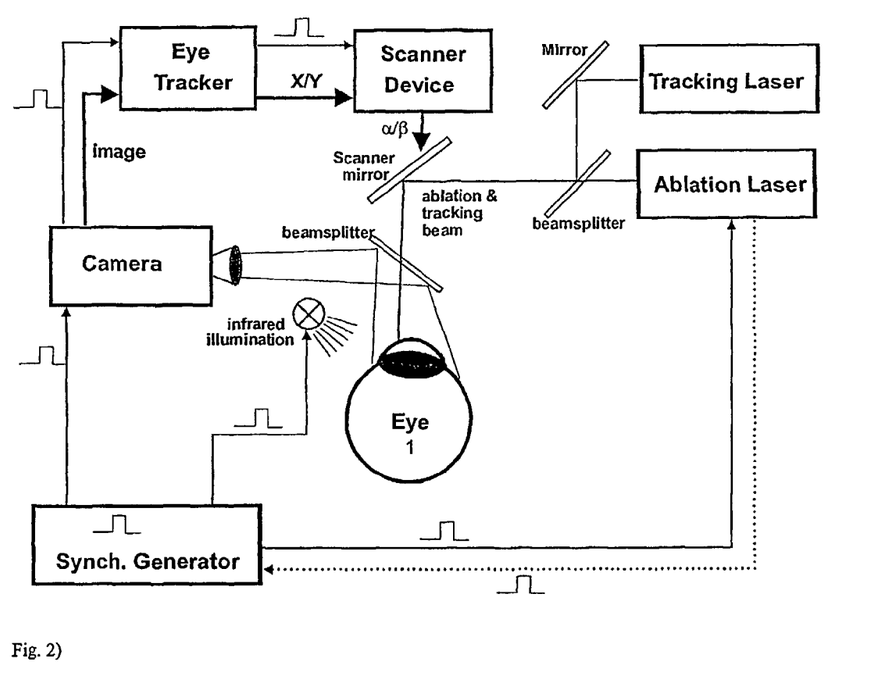
FIG. 2) Schematic set-up and processing scheme of preferred embodiment

FIG. 2 summarizes the preferred embodiment of the invention: The eye to be treated is illuminated by a pulsed light source—preferably infrared LEDs or laser diodes with beam shaping optics like collimator lenses and diffusers—that receives the on/off signal by a synchronisation signal generator. Light reflected by the eye is coupled out from the light path by a beam splitter towards the camera. This camera acquires the image with an interline sensor, a CCD- or CMOS-chip that allows independent image acquisition and image transfer. Nevertheless, other camera types could be used as well, such as standard video or high-speed cameras. Start of the image acquisition (exposure) is controlled by the synchronisation signal generator. After image acquisition the image is then transferred to the eye tracker, which determines the eye position and the ablation position of the previous shot on the eye. The scanner device is then supplied with the measured eye co-ordinates (x/y) that are transformed into angles ($\alpha/\beta$) for the scanner mirrors in order to direct the ablation beam onto the intended position on the eye. After receiving a synchronisation signal from the synchronisation signal generator the laser applies the ablation shot onto the eye. An infrared tracking laser beam, which is coaxially aligned to the ablation laser beam (using a mirror and a beam splitter, transparent for the ablation beam), documents the true ablation position on the eye, which is then corrected for in a later laser shot.

The timing relation of image acquisition, illumination, image processing, laser position control and laser firing is controlled by the synchronization signal generator.

Timing Scheme

Figure 3:
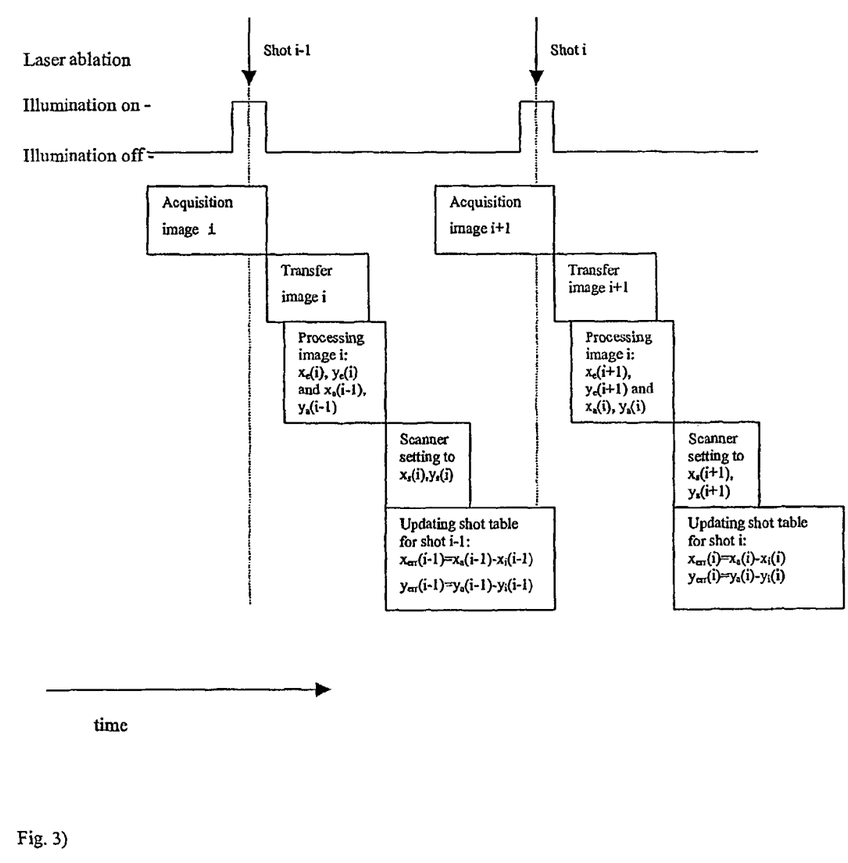
FIG. 3) Timing scheme of processing in accordance with a preferred embodiment.

A more detailed insight into the present invention can be given with a timing scheme, shown in FIG. 3, as the timing and order of actions forms a significant part of the invention:

Timing of the whole system is controlled by the synchronisation signal generator, that supplies the synchronisation signal to the imaging sensor (CCD- or CMOS-chip) within the camera, to the illumination and to the laser device. Since some lasers are not capable of operating with an external synchronisation the synchronisation signal might also be controlled or supplied by the laser device itself, as indicated in FIG. 2 (dotted arrow).

After calculation of the ablation profile and generation of the shot table the treatment procedure is started with the image integration time of the CCD- or CMOS-chip (image exposure) to gather an image of the eye (image 1). The—preferably infrared—illumination is only turned on during the end of the exposure time, reducing the effective exposure time of the imaging sensor, thus minimising the delay until image transfer (see FIG. 8*a* for details). After image acquisition the image is then transferred line by line to the eye tracker. Having received the first line of the image (image 1) the eye tracker already starts to process the image to determine the eye position (eye co-ordinates $x_e(1)$, $y_e(1)$). Each line is directly processed after being transferred to the eye tracker. After transferring and processing the last line of the image, the eye tracker performs final computations and sends the determined eye co-ordinates ($x_e(1)$, $y_e(1)$) to the scanner device.

Due to the overlap of image transfer and image processing ("ontime processing") the effective image processing time can be reduced to the processing time for one line plus the time required to finalize computations. The scanner device utilizes the eye co-ordinates ($x_e(1)$, $y_e(1)$) as an offset to determine the shot co-ordinates ($x_s(1)$, $y_s(1)$) of the laser in the laser device's co-ordinate system by adding the intended shot co-ordinates ($x_i(1)$, $y_i(1)$), i.e. $x_s(1)=x_e(1)+x_i(1)$ and $y_s(1)=y_e(1)+y_i(1)$. Since most scanners devices adjust the laser beam by rotating scanner mirrors, the shot co-ordinates ($x_s(1)$, $y_s(1)$) are transformed into corresponding angles $\alpha(1)$, $\beta(1)$. After the scanner mirrors are set to these angles, the laser shot (shot 1) can be applied. Due to synchronization this shot (shot 1) is applied during exposure time of the subsequent image (image 2). This coincidence enables a determination of the actual shot co-ordinates $x_a(1)$, $y_a(1)$ relative to the eye position $x_e(2)$, $y_e(2)$ at the time image 2 is acquired and the resulting positioning errors $x_{err}(1)=x_a(1)-x_i(1)$ and $y_{err}(1)=y_a(1)-y_i(1)$. The errors are determined during processing of image 2 and are used to update the shot table for subsequent shots as described in greater detail later on.

In general, shot i is applied during image acquisition of image i+1 with the shot co-ordinates $x_s(i)$, $y_s(i)$. Therefore the positioning error $x_{err}(i)$ of shot i is determined from image i+1. Due to the processing time the shot table can be updated for errors of shot i after shot i+1 has been applied.

Supplying the same frequency for the eye-tracking system and the ablation laser avoids non-constant overall delay times. Furthermore, coincidence of image acquisition and laser ablation provides the possibility to establish an error correction method, since the actual laser ablation position is documented with an image.

A) Error Determination and Correction

With an error-correction procedure the importance of delay decreases drastically. Here we establish the opportunity for error-correction by providing methods to estimate or measure occurring positioning errors:

i) Ablation Positioning Error Estimation

Figure 6:
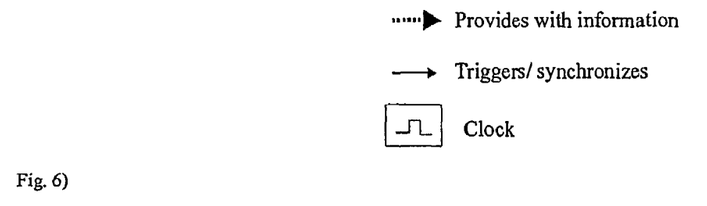
FIG. 6) Schematic block diagram for the different synchronization
Figure 6A:
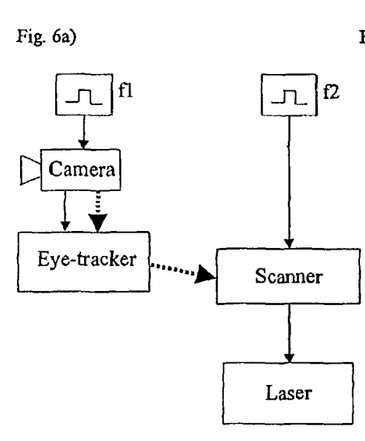
Figure 6B:
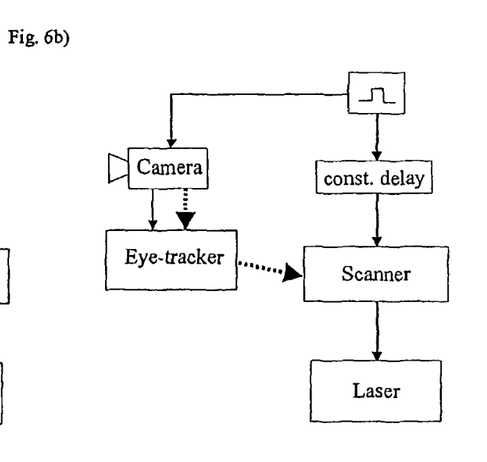
Figure 6C:
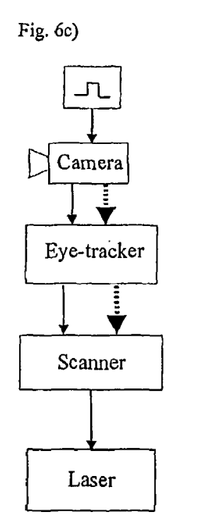
Figure 6D:
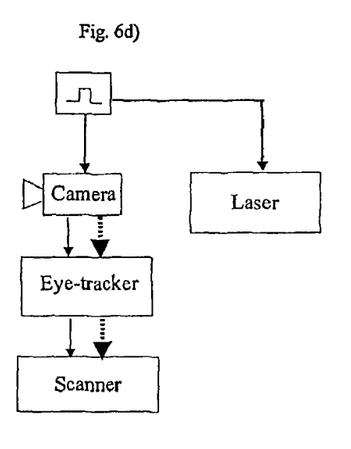
Figure 7B:
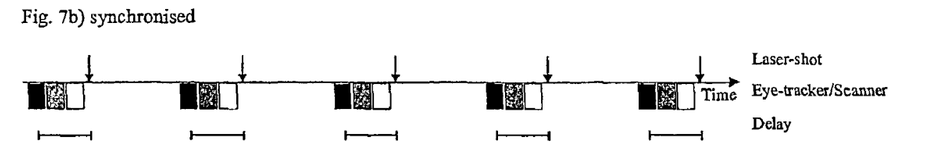
Figure 7C:
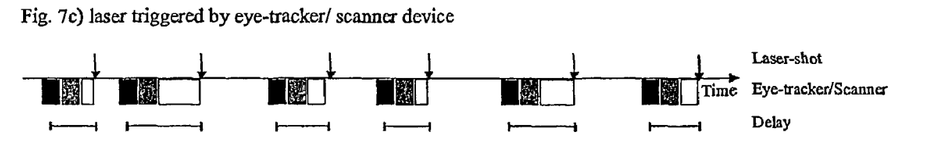
Figure 7D:
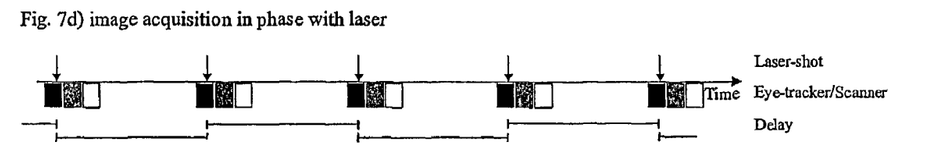

By synchronizing laser shots and image acquisition without a temporal shift, i.e. coincidence of laser shot and image acquisition, an eye image (image i) is obtained with a known setting of the positioning device using the intended laser ablation position ($x_i(i-1)$, $y_i(i-1)$), and the compensating eye position ($x_e(i-1)$, $y_e(i-1)$), obtained from a previous image (image i−1). One possibility is to trigger the laser by the camera, as shown in FIG. 6*d*). The resulting timing scheme is displayed in FIG. 7*d*).

Image processing of the current image (image i) obtains the eye position ($x_e(i-1)$, $y_e(i-1)$) at the time of the shot i−1. If the eye has moved between the previous image i−1 and the current image i the positioning error can be calculated by the difference of the eye's current position ($x_e(i)$, $y_e(i)$) and previous eye position ($x_e(i-1)$, $y_e(i-1)$). The estimated ablation position can be calculated by adding this difference to the intended ablation position.

Both, the estimate of the ablation position and the ablation error are also very useful for documentation purposes, quality control or future improvements of the treatment procedure. Furthermore it is also useful information for online diagnostics like online topometry or online pachymetry.

ii) Tracking-Laser for Measurement of Laser Positioning

Figure 4:
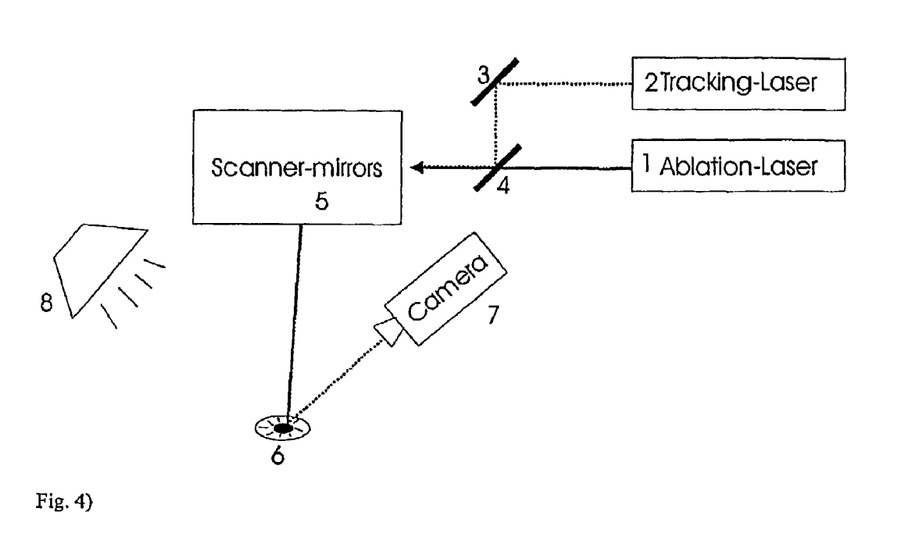
FIG. 4) Schematic diagram of the light path of the tracking laser

The apparatus illustrated in FIG. 4 provides an actual measurement of the ablation position and positioning errors during refractive surgery: In addition to the ablation laser (1) the beam of a tracking laser (2) is inserted coaxially into the optical path of the ablation laser utilizing mirrors (3) and (4) with (4) being transparent for the ablation laser wavelength. The tracking laser operates at a wavelength typically in the infrared or visible range that can be captured by the observing camera (7) of the eye tracker in fixed laser co-ordinates. Because no changes are made to the rest of the optical path (5), both laser beams hit the cornea (6) at the same position. The camera (7) acquires, coincidental with the laser shot, an image of the eye (illuminated with visible or infrared light (8)) together with the reflection from the tracking laser on the cornea. Utilizing image processing the eye position (i.e. determining the centre of the pupil or iris) and the tracking laser position (i.e. determining the centre of the reflection from the laser on the cornea) is measured relative to the fixed laser system by the eye tracker. The difference between both measurements provides a true ablation position on the eye or the cornea.

Comparing the intended ablation position with the actual laser position yields to the positioning error.

Generally, other implementations or embodiments or combinations thereof of this invention are possible, such as:

The illumination is not restricted to the infrared domain. Other wavelengths, such as visible light or combinations could be used as well.

An alternative to the pulsed illumination is a shutter at the camera, that also limits the effective exposure time. A combination thereof would also be a possible embodiment with the advantage to easily control the amount of light falling onto the patient's eye by pulsation and to control effective exposure time with the shutter.

The imaging device could be a CCD- or CMOS camera or even a line sensor etc. The reduction of delay due to synchronisation is even not restricted to imaging systems: electrooculography or scleral coils are further possible eye position measurement devices.

iii) Error Correction Methods

Figure 5:
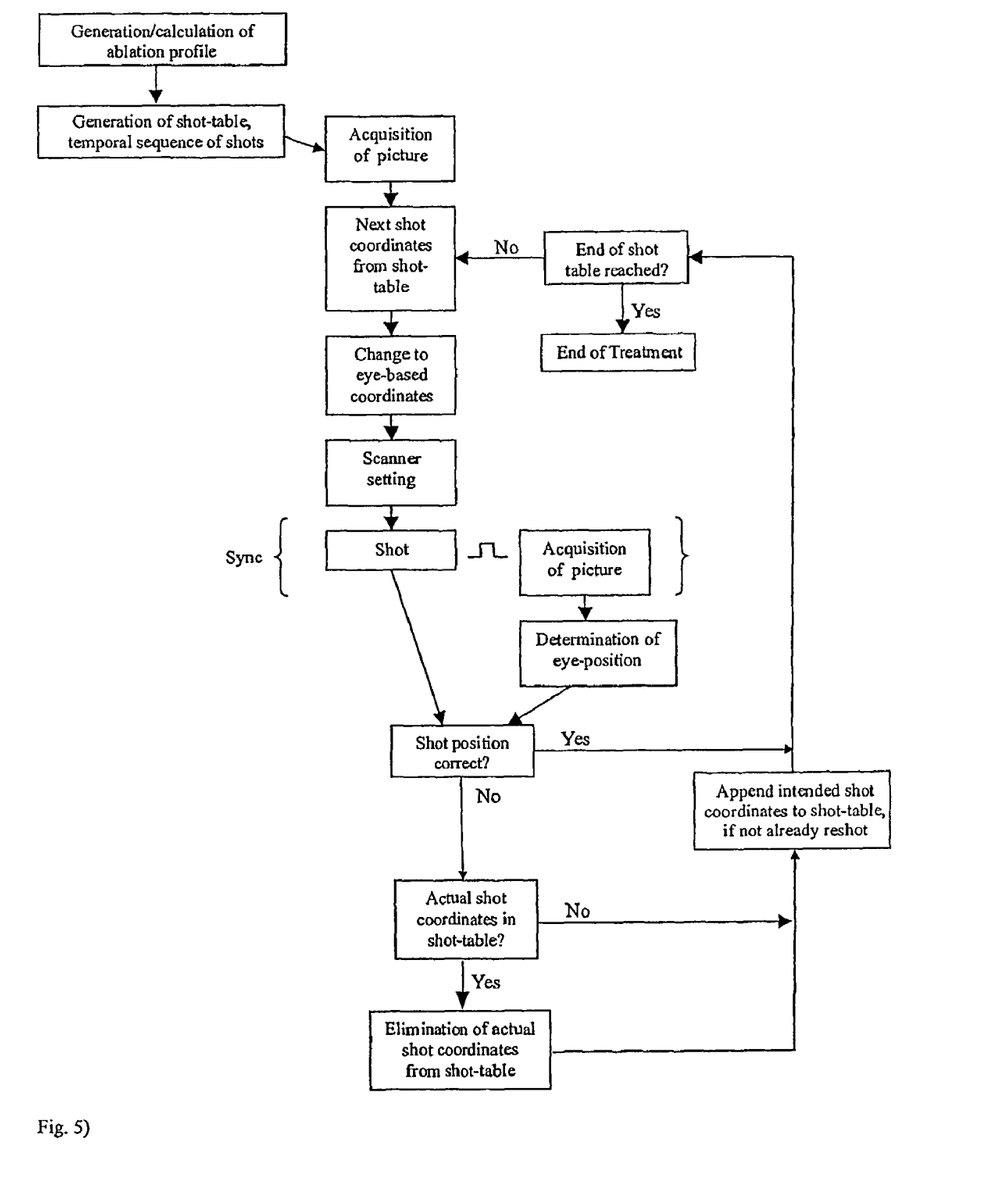
FIG. 5) Flow diagram of an advanced procedure for laser refractive surgery, including error correction.

The availability of an estimate or measurement of the ablation position on the eye and computing the positioning errors allows a further decrease of these errors by dynamic modification of the shot table, as summarized in FIG. 5:

This processing scheme offers several ways or combinations thereof, for error correction in case of a deviation from the intended ablation position occurred:

i) Re-shooting to the original intended co-ordinates, e.g. performing an ablation at the same eye-based co-ordinates, since the previous shot missed the target position. This could be inserted immediately or by appending this shot to the end of the shot-table. If during the repeated laser shot a significant positioning error occurs again, further replications may be omitted to guarantee a secure termination.

ii) Because of the large number of shots necessary for the complete ablation process, it is quite likely, that a misled shot has caused an ablation on the cornea at a position, or at least in close neighbourhood of a position that should be a result of a future laser shot. Therefore, the remaining shot-table could be searched for this position. If an entry in the shot-table with approximately these co-ordinates exists, it is omitted from the following processing. This avoids an additional ablation at the identical position.

The fact has to be stressed, that one misplaced shot introduces two errors into the ablation treatment: One occurs, because the laser does not hit the cornea at the intended position, the other error occurs, because the laser does hit the cornea at a different position. With the above methods, the first error can always be compensated for, and the second error only in the case if the accidental shot co-ordinates are to be shot in later processing.

In combination with online diagnostics like online topometry or online pachymetry, this invention could be upgraded to actually measure ablation error and correct for this error.

B) Delay Reduction:

The overall delay time, consisting of PROCESSING DELAY and SYNCHRONISATION DELAY and the resulting positioning errors can be reduced through synchronisation of the involved devices, e.g. the eye-tracking system and the ablating laser:

i) Minimisation of Synchronisation Delay

Supplying the same frequency for the eye-tracking system and the ablation laser avoids non-constant overall delay times. With the phase-shift between image acquisition and laser-shot set to the maximal possible Processing Delay, on average a reduction of the Synchronisation Delay can be obtained by avoiding the longest Synchronisation Delay times. A possible synchronisation scheme and the resulting time scheme is displayed in FIGS. 6b and 7b. By comparing the timing schemes of synchronized (FIG. 7b) and non-synchronized (FIG. 7a) setups it becomes clear that synchronisation circumvents the extraordinary long delays in the unsynchronized set, i.e. those cases, where the overall delay time is longer than the time between image acquisition and following laser shot. In these cases, the latest available eye co-ordinates are "older" than the actual processing delay.

In the general case constant overall delay times can be reached if the laser shot interval is an integer multiple of the sampling interval for eye tracking.

An alternative way of synchronisation offers the possibility to almost eliminate Synchronisation Delay. This is done by the synchronisation signal generator triggering the eye-tracker, which in return triggers the positioning device after image processing and by the synchronisation generator triggering the laser after exact adjustment as outlined in FIG. 6c). The main purpose here is to decrease delay whenever possible. This meets the fact that eye tracking itself depends on the complexity of the input, thus leading to different image processing durations, and the time required for adjusting the positioning device normally depends on the distance to overcome on the cornea. The resulting timing-scheme is displayed in FIG. 7c). This special form of synchronisation therefore reduces the overall delay by reducing the (variable) delay components to the amount of delay they actually need for processing and not to the maximal possible delay that might occur.

ii) Minimisation of Processing Delay by Reduction of Effective Exposure Time

Besides the minimization of the SYNCHRONIZATION DELAY a minimization of PROCESSING DELAYS lead to a decrease of the overall delay and therefore to a decrease of positioning errors:

With a pulsed illumination, synchronized in a way that the eye is illuminated at the end of the image acquisition (=integration time of the CCD- or CMOS-camera) with high intensity, the (effective) exposure is shifted towards the end of image acquisition, leading to a shorter PROCESSING DELAY. The reason for this reduction is that the actually acquired image results a time at the end of the image acquisition time and therefore the duration between the image and the time the shot is applied is shorter. This duration is equivalent to the processing delay. The timing scheme is displayed in FIG. 8a).

Figures 8, 8A, 8B:
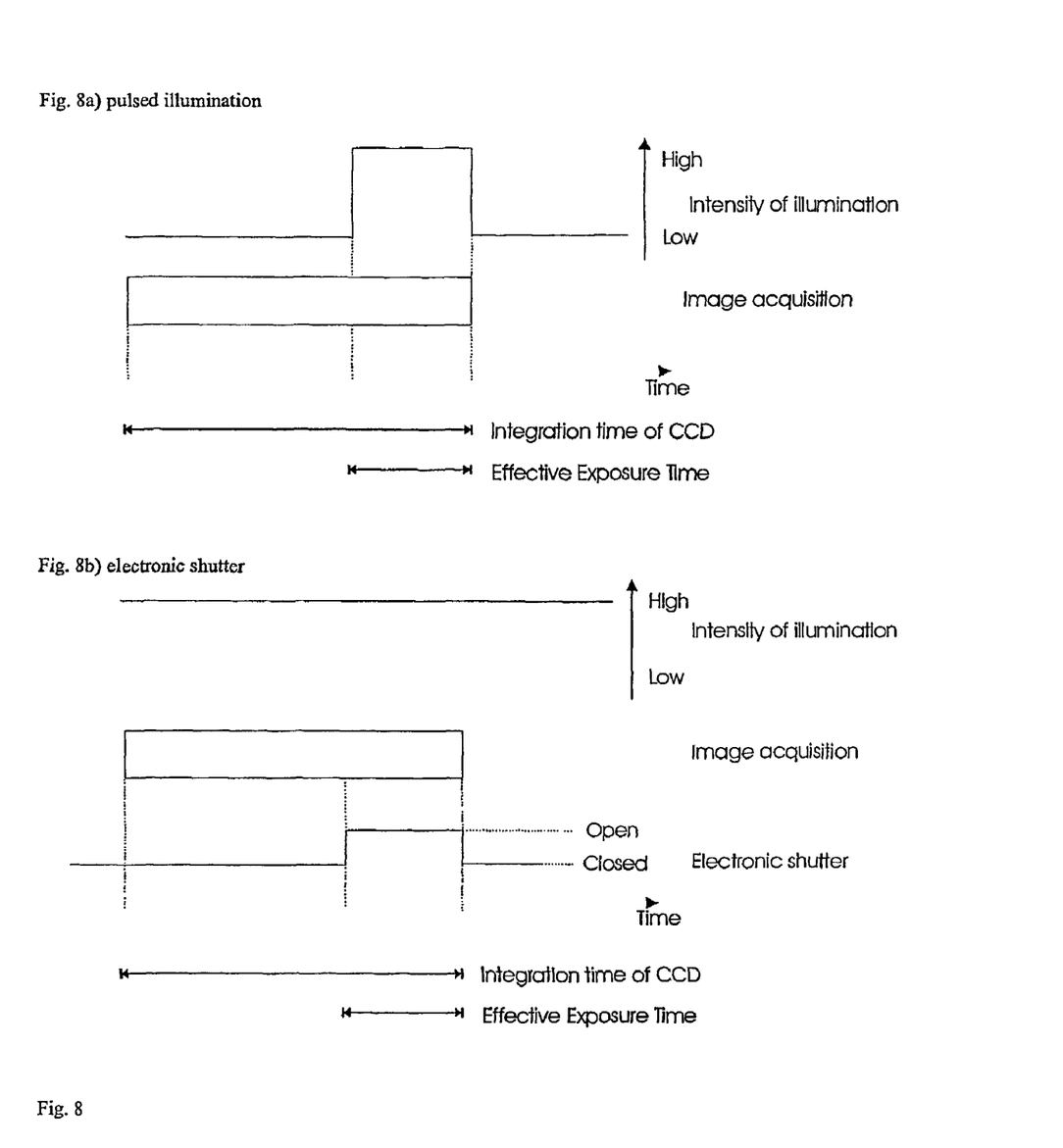
FIG. 8) Timing scheme for reduction of exposure time by utilizing a pulsed illumination (a) and by utilizing an electronic shutter (b).

An equivalent result is obtained by use of a (not necessarily constant) illumination with high intensity in combination with an electronic shutter, i.e. a device that reduces the effective integration time, as shown in FIG. 8b). This produces the same shift towards the end of image acquisition and again a shorter PROCESSING DELAY.

Both methods have in common that the intensity of illumination has to be increased in order to keep the amount of light constant that is captured for each image. However, care has to be taken to keep the intensities in a medically acceptable range. Further these methods have the advantageous side effects to avoid blurred images because of eye movements and to lead towards a more precise definition of the exposure time.

Various combinations of the described methods and the apparatus are possible as well as there exist many different ways to implement or embody them, only differing in details. Therefore we claim:

1. In combination with a refractive laser system and an eye-tracking system, an apparatus comprising a synchronization signal generator in combination with the refractive laser system and the eye-tracking system and which is connected to the refractive laser system and to the eye-tracking system, said synchronization signal generator providing a synchronization signal to the refractive laser system triggering an ablation shot onto the eye being treated, and providing a synchronization signal to the eye-tracking system triggering image acquisition, and wherein the synchronization signal generator is configured so that the generation of the synchronization signal occurs in accordance with a timing scheme and is used to synchronize said ablation shot and said image acquisition.

2. In combination with a refractive laser system used for eye surgery, an apparatus comprising:

an eye-tracking system provided with an imaging device for acquiring an image of an eye being treated;

a synchronization signal generator which is connected to the refractive laser system and to the eye-tracking system, which provides a synchronization signal to the refractive laser system triggering an ablation shot onto the eye being treated, and which provides a synchronization signal to the eye-tracking system triggering image acquisition, and wherein the synchronization signal generator is configured for the generation of the synchronization signals in accordance with a timing scheme to synchronize said ablation shot and said image acquisition.

3. The apparatus according to claim 1 or 2 wherein the timing scheme is adapted such that the image acquisition and the laser ablation occur coincidentally.

4. The apparatus according to claim 1 or 2 wherein the timing scheme is adapted such that the phase-shift between image acquisition and laser ablation is set to the maximal possible delay caused by image processing.

5. The apparatus according to claim 1 or 2 wherein the timing scheme is adapted such that the laser ablation interval is an integer multiple of the sampling interval for eye tracking.

6. The apparatus according to claim 1 or 2 wherein the timing scheme is adapted such that the laser ablation is triggered after the image processing is completed and a scanning device has been positioned.

7. The apparatus according to claim 2 wherein an imaging device for acquiring an image of the eye being treated is provided in the form of a CCD- or CMOS camera or a standard video or high-speed camera or an interline sensor that allows independent image acquisition and image transfer.

8. The apparatus according to claim 1 or 2 wherein an imaging device for eye position measurement is provided in the form of a line sensor.

9. The apparatus according to claim 3 wherein eye-tracking system comprises a tracking laser for measurement of the laser ablation positioning.

10. The apparatus according to claim 2 wherein the eye-tracking system or laser system comprises an error correction method, which utilizes an eye position obtained by the eye tracking system and an estimate or measurement of an actual ablation position on the eye to derive an error as a difference between an intended laser position an actual laser position which is calculated after laser firing to compensate for errors made during surgery.

* * * * *